United States Patent
Ates et al.

(10) Patent No.: US 8,076,493 B2
(45) Date of Patent: Dec. 13, 2011

(54) 3-CARBOXY-2-OXO-1-PYRROLIDINE DERIVATIVES AND THEIR USES

(75) Inventors: Celal Ates, Louvain-la-Neuve (BE); Arnaud Schule, Braine-l'Alleud (BE)

(73) Assignee: UCB Pharma, S.A., Brussels (BE)

( * ) Notice: Subject to any disclaimer, the term of this patent is extended or adjusted under 35 U.S.C. 154(b) by 627 days.

(21) Appl. No.: 12/096,257

(22) PCT Filed: Dec. 5, 2006

(86) PCT No.: PCT/EP2006/011668
§ 371 (c)(1),
(2), (4) Date: Sep. 18, 2008

(87) PCT Pub. No.: WO2007/065634
PCT Pub. Date: Jun. 14, 2007

(65) Prior Publication Data
US 2009/0012313 A1  Jan. 8, 2009

(30) Foreign Application Priority Data
Dec. 7, 2005 (EP) .................................... 05026694

(51) Int. Cl.
*C07D 207/27* (2006.01)
*C07D 207/20* (2006.01)
(52) U.S. Cl. .................. 548/531; 548/550; 548/551
(58) Field of Classification Search .................. 548/530, 548/550, 551
See application file for complete search history.

(56) References Cited

U.S. PATENT DOCUMENTS

| 4,118,396 | A  |   | 10/1978 | Pifferi et al. |          |
|-----------|----|---|---------|----------------|----------|
| 5,340,802 | A  |   | 8/1994  | Shiosaki et al.|          |
| 6,784,197 | B2 | * | 8/2004  | Differding et al. | 514/365 |
| 7,612,215 | B2 | * | 11/2009 | Lurquin et al. | 548/550  |

FOREIGN PATENT DOCUMENTS

| EP | 0342613 A | 11/1989 |
|----|-----------|---------|
| EP | 0405506 A | 1/1991 |
| GB | 1323061 | * 7/1973 |
| WO | 2005-028435 A | 3/2005 |

OTHER PUBLICATIONS

Kenda et al, Discovery of 4-Substituted Pyrrolidone Butanamides as New Agents with Significant Antiepileptic Activity, Journal of Medicinal Chemistry, 2004, 47(3), p. 530-549.*
Freidiner, Synthesis of gamms-lactam-constrained tryptophyl-lysine derivatives, 1985, Journal of Organic Chemistry, 50(19), p. 3631-3633.*
Barluenga, Joset, et al., "First Highly Regio- and Diastereoselective [3+2] Cycloaddition of Chiral Nonracemic Fischer Carbene Complexes with Azomethine Ylides: An Enantioselective Synthesis of (+)-Rolipram," Journal of Organic Chemistry, 2001, vol. 7, No. 16, pp. 3533-3544.
Galeazzi, R., et al., "From Pyrrolidin-2-Ones to 3-Aza-2-Oxobicyclo[3.2.0]heptanes. Synthesis of Both Enantiomers of cis-2-Aminomethylcyclobutane Carboxylic Acid, a Conformationally Restricted Analogue of GABA," Tetrahedron, Elsevier Science Publishers, 1999, vol. 55, No. 1, pp. 261-270.

* cited by examiner

*Primary Examiner* — Andrew D Kosar
*Assistant Examiner* — Karen Cheng
(74) *Attorney, Agent, or Firm* — McDonnell Boehnen Hulbert & Berghoff LLP

(57) ABSTRACT

The present invention relates to 3-carboxy-2-oxo-1-pyrrolidine derivatives of formula (I), geometrical isomers, enantiomers, diastereoisomers, pharmaceutically acceptable salts and all possible mixtures thereof, and processes using them.

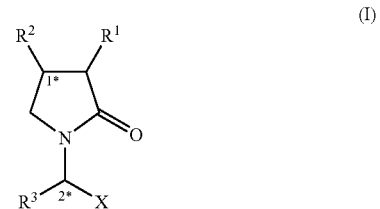

30 Claims, No Drawings

3-CARBOXY-2-OXO-1-PYRROLIDINE DERIVATIVES AND THEIR USES

This application is a US national phase of International Application Number PCT/EP2006/011668 filed on Dec. 5, 2006, which claims priority to European Application Number EP 05026694.9, filed on Dec. 7, 2005, the disclosure of which is incorporated herein by reference.

The present invention relates to 3-carboxy-2-oxo-1-pyrrolidine derivatives and processes using them.

European Patent No. 0 162 036 B1 discloses compound (S)-α-ethyl-2-oxo-1-pyrrolidine acetamide, which is known under the International Non-proprietary Name of Levetiracetam.

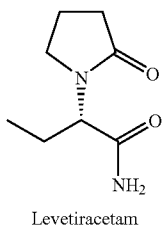

Levetiracetam

Levetiracetam is disclosed as a protective agent for the treatment and prevention of hypoxic and ischemic type aggressions of the central nervous system in European patent EP 0 162 036 B1. This compound is also effective in the treatment of epilepsy.

The preparation of Levetiracetam has been disclosed in European Patent No. 0 162 036 and in British Patent No. 2 225 322.

International patent application having publication number WO 01/62726 discloses 2-oxo-1-pyrrolidine derivatives and methods for their preparation. It particularly discloses compound (2S)-2-[(4R)-2-oxo-4-propyl-pyrrolidin-1-yl]butanamide known under the international non propriety name of brivaracetam.

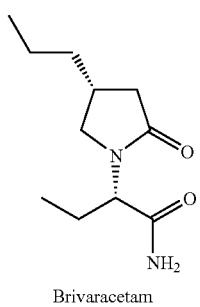

Brivaracetam

International patent application having publication number WO 2005/121082 describes a process of preparation of 2-oxo-1-pyrrolidine derivatives and particularly discloses a process of preparation of (2S)-2-[(4S)-4-(2,2-difluorovinyl)-2-oxo-pyrrolidin-1-yl]butanamide known under the international non propriety name of seletracetam.

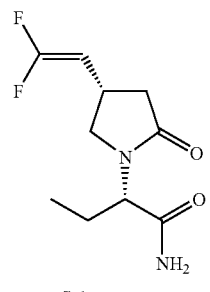

Seletracetam

Kenda et al., in J. Med. Chem. 2004, 47, 530-549, describe processes of preparation of 2-oxo-1-pyrrolidine derivatives and particularly discloses compound 1-((1S)-1-carbamoyl-propyl)-2-oxo-pyrrolidone-3-carboxylic acid as a synthetic intermediate.

U.S. Pat. No. 5,340,802 and European patent application published under number EP 0 405 506 A1 disclose 2(S)(3-carboxy-2-oxo-1-pyrrolidinyl)-4-methyl pentanoic acid as synthetic intermediate in the synthesis of peptide compounds.

We have now surprisingly found that 3-carboxy-2-oxo-1-pyrrolidine derivatives are useful for the synthesis of 2-oxo-1-pyrrolidine derivatives.

In a first aspect, the present invention relates to a compound of formula (I), geometrical isomers, enantiomers, diastereoisomers, and all possible mixtures thereof,

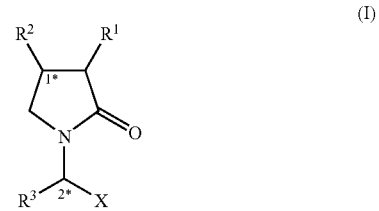

wherein,
$R^1$ is COOH, —COOM or —COOR$^4$,
$R^2$ is hydrogen or $C_{1-10}$ alkyl,
$R^3$ is $C_{1-10}$ alkyl or $C_{2-6}$ alkenyl,
X is —CONR$^5$R$^6$, —COOH, —COOR$^4$ or —CN,
M is an alkali metal,
$R^4$ is $C_{1-10}$ alkyl,
$R^5$ is hydrogen or $C_{1-10}$ alkyl,
$R^6$ is hydrogen or $C_{1-10}$ alkyl,
provided that compound of formula (I) is different from 1-((1S)-1-carbamoyl-propyl)-2-oxo-pyrrolidone-3-carboxylic acid and from 2(S)(3-carboxy-2-oxo-1-pyrrolidinyl)-4-methyl pentanoic acid.

The term "alkyl", as used herein, is a group which represents saturated, monovalent hydrocarbon radicals having straight (unbranched), branched or cyclic moieties, or combinations thereof. Preferred alkyl comprises 1 to 10 carbons. More preferred alkyl comprises 1 to 4 carbons. Optionally, alkyl groups may be substituted by 1 to 5 substituents independently selected from the group consisting of halogen, hydroxy, alkoxy, ester, acyl, cyano, acyloxy, acid, amide or amino group. Preferred alkyl groups are methyl, ethyl, n-propyl, trifluoromethyl and trifluoroethyl.

The term "alkenyl" as used herein represents unsubstituted or substituted branched, unbranched or cyclic hydrocarbon radicals or combinations thereof having at least one double bond. Preferred alkenyl comprises 2 to 6 carbons. More preferred alkenyl comprises 2 to 4 carbons. "Alkenyl" moieties may be optionally substituted by 1 to 5 substituents independently selected from the group consisting of halogen, hydroxy, alkoxy, ester, acyl, cyano, acyloxy, carboxylic acid, amide or amino group.

The term "halogen", as used herein, represents an atom of fluorine, chlorine, bromine, or iodine.

The term "hydroxy", as used herein, represents a group of formula —OH.

The term "alkoxy", as used herein, represents a group of formula $OR^a$ wherein $R^a$ is $C_{1-4}$ alkyl as defined above.

The term "acyl" as used herein, represents a group of formula $R^bCO$—, wherein $R^b$ represents a $C_{1-4}$ alkyl as defined above.

The term "ester", as used herein, represents a group of formula —$COOR^c$ wherein $R^c$ represents a $C_{1-4}$ alkyl as defined above.

The term "cyano" as used herein represents a group of formula —CN.

The term "acyloxy" as used herein represents a group of formula —O—$COR^d$, wherein $R^d$ is a $C_{1-4}$ alkyl as defined above or an aryl group.

The term "aryl" as used herein, represents an organic radical derived from an aromatic hydrocarbon by removal of one hydrogen, for example a phenyl.

The term "carboxylic acid" as used herein represents a group of formula —COOH.

The term "amino group", as used herein, represents a group of formula —$NH_2$, $NHR^e$ or $NR^fR^e$ wherein $R^e$ and $R^f$ are alkyl groups as defined above in the specification.

The term "amide", as used herein, refers to a group of formula —$NH_2$—CO—, —$NHR^g$—CO, or —$NR^gR^h$—CO, wherein $R^g$ and $R^h$ are alkyl groups as defined above in the specification.

The term "alkali metal" as used herein refers to an element selected from group I of the periodic table of elements. Preferred alkali metal is Na.

Preferably, $R^1$ is —COOH or —$COOR^4$, wherein $R^4$ is a $C_{1-10}$ alkyl.

In one embodiment according to the present invention, $R^1$ is —COOH or —$COOR^4$, wherein $R^4$ is a $C_{1-4}$ alkyl. In another embodiment according to the present invention, $R^1$ is —COOH or —COOMe.

In one embodiment according to the present invention, $R^2$ is hydrogen or $C_{1-4}$ alkyl. In another embodiment according to the present invention, $R^2$ is hydrogen or n-propyl.

In one embodiment according to the present invention, $R^3$ is $C_{1-4}$ alkyl. In another embodiment according to the present invention, $R^3$ is ethyl.

In one embodiment according to the present invention, X is —$CONR^5R^6$, —COOH or —$COOR^4$, wherein $R^4$ is a $C_{1-4}$ alkyl. In another embodiment according to the present invention, X is —$CONR^5R^6$.

In one embodiment according to the present invention, $R^5$ is hydrogen or $C_{1-4}$ alkyl. In another embodiment according to the present invention, $R^5$ is hydrogen.

In one embodiment according to the present invention, $R^6$ is hydrogen or $C_{1-4}$ alkyl. In another embodiment according to the present invention, $R^6$ is hydrogen.

In one embodiment, the present invention relates to a compound of formula (I), geometrical isomers, enantiomers, diastereoisomers, and all possible mixtures thereof,

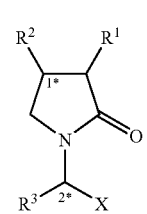

(I)

wherein
$R^1$ is —COOH or —$COOR^4$,
$R^2$ is hydrogen or $C_{1-4}$ alkyl,
$R^3$ is $C_{1-4}$ alkyl,
X is —$CONR^5R^6$, —COOH or —$COOR^4$
$R^4$ is a $C_{1-4}$ alkyl,
$R^5$ is hydrogen or $C_{1-4}$ alkyl,
$R^6$ is hydrogen or $C_{1-4}$ alkyl,
provided that compound of formula (I) is different from 1-((1S)-1-carbamoyl-propyl)-2-oxo-pyrrolidone-3-carboxylic acid and from 2(S)(3-carboxy-2-oxo-1-pyrrolidinyl)-4-methyl pentanoic acid.

In another embodiment, the present invention relates to a compound of formula (I), geometrical isomers, enantiomers, diastereoisomers, and all possible mixtures thereof,

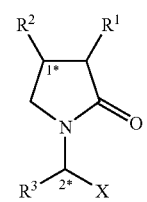

(I)

wherein
$R^1$ is COOH or —COOMe,
$R^2$ is hydrogen or n-propyl,
$R^3$ is ethyl,
X is —$CONH_2$,
provided that compound of formula (I) is different from 1-((1S)-1-carbamoyl-propyl)-2-oxo-pyrrolidone-3-carboxylic acid.

Examples of compounds of formula (I) according to the present invention are (R)-1-((S)-1-Carbamoyl-propyl)-2-oxo-4-propyl-pyrrolidine-3-carboxylic acid (Id), 1-((S)-1-Carbamoyl-propyl)-2-oxo-pyrrolidine-3-carboxylic acid methyl ester (Ih) and (R)-1-((S)-1-Carbamoyl-propyl)-2-oxo-4-propyl-pyrrolidine-3-carboxylic acid methyl ester (If).

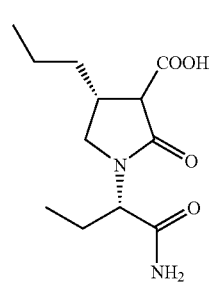

(Id)

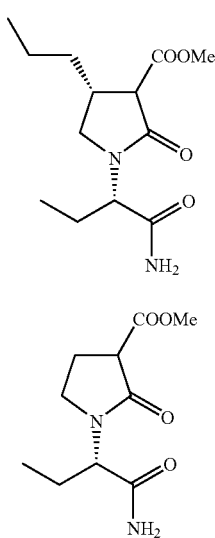

Compounds of formula (I) may be synthesized by reacting a compound of formula (II) with a compound of formula (III) according to the following scheme (scheme 1).

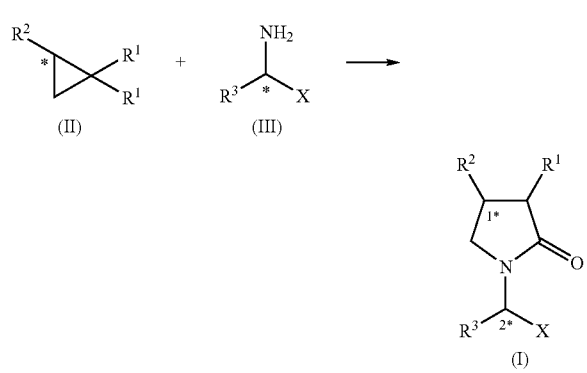

Alternatively compounds of formula (I) may be prepared according to the method described by R. M. Freidinger in J. Org. Chem. 1985, 50, 3631-3633 or by Kenda et al. in J. Med. Chem. 2004, 47, 530-549, wherein compound of formula (IIa) is reacted with compound of formula (III) to afford compound of formula (I).

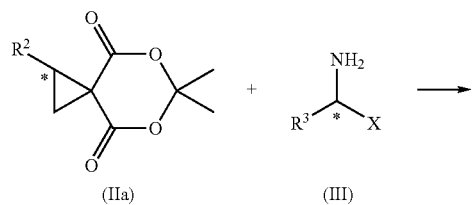

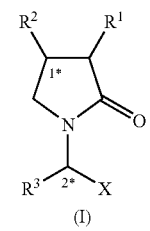

Compounds of formula (I) may also be synthesized according to any other conventional method known to the person skilled in the art.

According to one embodiment of the present invention, $R^1$ is —COOH or —COOR$^4$ $R^4$ is $C_{1-10}$ alkyl, and $R^2$ is hydrogen or $C_{1-10}$ alkyl in compounds of formula (II) and (IIa).

According to one embodiment of the present invention, $R^3$ is $C_{1-10}$ alkyl or $C_{2-6}$ alkenyl, X is —CONR$^5$R$^6$, —COOR$^4$ or —CN, $R^4$ is $C_{1-10}$ alkyl, $R^5$ is hydrogen or $C_{1-10}$ alkyl, $R^6$ is hydrogen or $C_{1-10}$ alkyl in compound of formula (III).

According to another embodiment of the present invention, $R^1$ is —COOH or —COOR$^4$, $R^4$ is $C_{1-4}$ alkyl and $R^2$ is hydrogen or $C_{1-4}$ alkyl in compounds of formula (II) and (IIa).

According to another embodiment of the present invention, $R^3$ is $C_{1-4}$ alkyl, X is —CONR$^5$R$^6$, —COOH or —COOR$^4$, $R^4$ is $C_{1-4}$ alkyl, $R^5$ is hydrogen or $C_{1-4}$ alkyl, $R^6$ is hydrogen or $C_{1-4}$ alkyl in compound of formula (III).

According to a further embodiment of the present invention, $R^1$ is —COOH or —COOMe and $R^2$ is hydrogen or n-propyl in compounds of formula (II) and (IIa).

According to a further embodiment of the present invention formula (III) is 2-amino-butyramide.

In a particular embodiment, compound of formula (II) and (IIa) are selected from the group consisting of cyclopropane-1,1-dicarboxylic acid dimethyl ester, (S)-2-propyl-cyclopropane-1,1-dicarboxylic acid dimethyl ester, 6,6-Dimethyl-5,7-dioxa-spiro[2.5]octane-4,8-dione and (S)-6,6-Dimethyl-1-propyl-5,7-dioxa-spiro[2.5]octane-4,8-dione.

In a particular embodiment according to the present invention compound of formula (III) is (S)-2-amino-butyramide.

Compound of formula (III) used in the process according to the invention may be obtained by any means suitable therefore. Compound (III) is preferably obtained by neutralisation of the corresponding salts, more preferably from the corresponding hydrochloride or tartaric acid salt, most preferably from the corresponding hydrochloride salt.

Compounds of formula (I) are particular useful for the synthesis of compound of formula (IV).

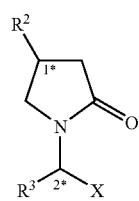

Particularly compounds of formula (I) are useful for the synthesis of Levetiracetam or Brivaracetam.

Thus, in a second aspect, the present invention relates to another process for the synthesis of compounds of formula (IV).

In one embodiment, the present invention relates to a process for the preparation of compounds of formula (IV), geometrical isomers, enantiomers, diastereoisomers, pharmaceutically acceptable salts and all possible mixtures thereof,

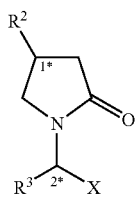
(IV)

said process comprising decarboxylation of a compound of formula (Ia), geometrical isomers, enantiomers, diastereoisomers, and all possible mixtures thereof,

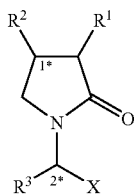
(Ia)

wherein
$R^1$ is —COOH or —COOM,
$R^2$ is hydrogen or $C_{1-10}$ alkyl,
$R^3$ is $C_{1-10}$ alkyl or $C_{2-6}$ alkenyl,
X is —CONR$^5$R$^6$, —COOH, —COOR$^4$ or —CN,
M is an alkali metal;
$R^4$ is $C_{1-10}$ alkyl;
$R^5$ is hydrogen or $C_{1-10}$ alkyl;
$R^6$ is hydrogen or $C_{1-10}$ alkyl.

Preferably, in second aspect of the invention, $R^1$ is —COOH

In another embodiment, the present invention relates to a process for the preparation of a compound of formula (IV), geometrical isomers, enantiomers, diastereoisomers, pharmaceutically acceptable salts and all possible mixtures thereof,

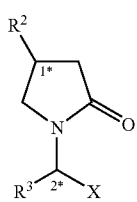
(IV)

said process comprising the decarbalkoxylation of compound of formula (Ib), geometrical isomers, enantiomers, diastereoisomers, and all possible mixtures thereof,

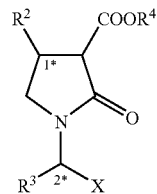
(Ib)

wherein
$R^2$ is hydrogen or $C_{1-10}$ alkyl,
$R^3$ is $C_{1-10}$ alkyl or $C_{2-6}$ alkenyl,
X is —CONR$^5$R$^6$, —COOH, —COOR$^4$ or —CN,
$R^4$ is $C_{1-10}$ alkyl,
$R^5$ is hydrogen or $C_{1-10}$ alkyl,
$R^6$ is hydrogen or $C_{1-10}$ alkyl.

The term "decarboxylation" as used herein means removal of a —COOH or —COOM moiety and replacement of said moiety by a hydrogen atom.

The term "decarbalkoxylation" as used herein means removal of a —COOR$^4$ moiety wherein R$^4$ is a $C_{1-10}$ alkyl and replacement of said moiety by a hydrogen atom.

Specific embodiments for X, $R^1$, $R^2$, $R^3$, $R^4$, $R^5$ and $R^6$ in second and third aspects of the present invention are the same as for the first aspect of the present invention.

Whilst some decarboxylation and decarbalkoxylation conditions have been described previously in the literature, when they are applied to compounds comprising an epimerisable chiral center, partial epimerisation at that chiral center may occur. Thus the desired decarboxylated or decarbalkoxylated product as well as its epimer may be obtained, thereby decreasing yield and productivity of the overall process, or precluding the overall industrial applicability of the process.

The present process is particularly advantageous since it can be applied industrially and allows obtention of compounds of formula (IV) with the desired configuration at its stereogenic center(s).

Decarboxylation of compound (Ia) is generally performed at atmospheric pressure in the presence of a solvent, for example a solvent having a boiling point greater than 110° C., such as toluene, dimethylformamide, dimethylsulfoxide, N-methyl-2-pyrrolidone (NMP), methylisobutylketone (MIBK).

In a particular embodiment the decarboxylation is performed with MIBK as solvent.

Typically, the decarboxylation is performed at a temperature ranging from 110° C. to 130° C. The reaction may occur at higher temperature but within said temperature range, risks of side reaction leading to degradation of the product are minimized.

In a particular embodiment according to the present invention the decarboxylation is performed at a temperature of 120° C.

The decarbalkoxylation of compound of formula (Ib) may be performed by any method suitable therefore. For example, the decarbalkoxylation may be performed directly according to the method described by A. P. Krapcho et al. in Tetrahedron Lett. 1967, 8, 215-217.

Alternatively, compound of formula (Ib) may be hydrolysed to afford compound of formula (Ia) which is subsequently decarboxylated as described here above.

The hydrolysis of compound of formula (Ib) into compound of formula (Ia) is generally performed in water or in a mixture of water and a solvent, such as methanol, ethanol, isopropanol, water or mixtures thereof. For example, hydrolysis is conducted in a mixture of water and methanol.

The hydrolysis of compound of formula (Ib) into compound of formula (Ia) is generally conducted in the presence of a base such as $K_2CO_3$, $Na_2CO_3$, NaOH or LiOH. For example, hydrolysis is performed in the presence of $K_2CO_3$.

Decarboxylation of compound of formula (Ia) or decarbalkoxylation of compound of formula (Ib) generally affords compound (IV) with a yield greater than 95%, preferably greater than 99%.

Compounds of formula (I) and compounds of formula (IV) have one or more stereogenic centers in their structure which are indicated by a number followed by an asterisk.

In one embodiment according to the present invention, compounds of formula (I) and of formula (IV) have two stereogenic centers indicated by (1*) and (2*). These stereogenic centers may be present in R or S configuration, said R and S notation being used in accordance with the rules described in Pure. Appl. Chem., 1976, 45, 11-30

In a particular embodiment according to the present invention compounds of formula (I) and of formula (IV) have the stereogenic center indicated by (1*) in the (S)- or in the (R)-form.

In another embodiment according to the present invention, compounds of formula (I) and of formula (IV) have the stereogenic center indicated by (1*) in the (R)-form.

In a particular embodiment according to the present invention compounds of formula (I) and of formula (IV) have the stereogenic center indicated by (2*) in the (S)- or in the (R)-form.

In another embodiment, compounds of formula (I) and of formula (IV) have the stereogenic center indicated by (2*) in the (S)-form.

The term "(S)-form", as used herein, means that more than 50%, preferably more than 90%, more preferably at least 95% of the compounds have the stereogenic carbon atom indicated by an asterisk in the S configuration.

The term "(R)-form", as used herein, means that more than 50%, preferably more than 90%, more preferably at least 95% of the compounds have the stereogenic carbon atom indicated by an asterisk in the R configuration.

Generally, the configuration of stereogenic centers present in compounds of formula (I) is retained during the decarboxylation or the decarbalkoxylation step of the process of preparation of compounds of formula (IV).

Thus, in a particular aspect, when applying the process of the present invention to compounds of formula (Ia) or (Ib) wherein stereogenic center indicated by (1*) is in the (R)-form, compounds of formula (IV) wherein stereogenic center indicated by (1*) is in the (R)-form are obtained.

In a further particular aspect, when applying the process of the present invention to compounds of formula (Ia) or (Ib) wherein stereogenic center indicated by (2*) is in the (S)-form, compounds of formula (IV) wherein stereogenic center indicated by (2*) is in the (S)-form are obtained.

Finding the appropriate conditions to achieve the latter is particularly difficult since stereogenic center (2*) in compounds of formula (Ia) and (Ib) bears a hydrogen atom which could epimerise under decarboxylation or decarbalkoxylation conditions described in the literature.

The process according to the present invention may optionally comprise a step of separation of the different diastereoisomers, particularly a step of separation of one or more of the different diastereoisomers of any of the compounds of formula (I), (Ia), (Ib) and (V).

Said separation may be achieved by liquid column chromatography or by recrystallisation according to conventional methods known to the person skilled in the art.

Retention of configuration of stereogenic centers mentioned here above advantageously reduces the number of separation and/or resolution steps in the overall process of preparation of compounds of formula (IV).

In a particular embodiment, the present invention relates to a process for the preparation of levetiracetam, said process comprising decarboxylation or decarbalkoxylation of compound of formula (Ic),

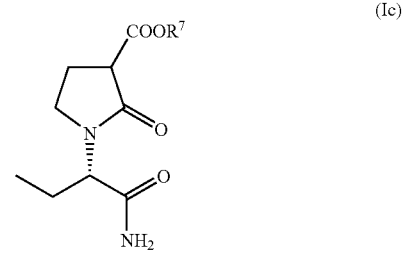

(Ic)

wherein $R^7$ is hydrogen, an alkali metal or $C_{1-10}$ alkyl.

Compound of formula (Ic) may be prepared according to any one of the methods described here above in the specification, such as methods described in schemes 1 and 2.

For example, when $R^7$ is hydrogen, compound of formula (Ic) may be obtained according to the method described in scheme 2 by reacting compound of formula (IIa) wherein $R^2$ is hydrogen with (S)-2-amino-butyramide.

In another particular embodiment, the present invention relates to a process for the preparation of brivaracetam, said process comprising decarboxylation or decarbalkoxylation of compound of formula (Id),

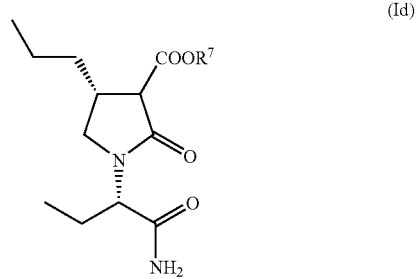

(Id)

wherein $R^7$ is hydrogen, an alkali metal or $C_{1-10}$ alkyl.

Compound (Id) may be prepared according to any one of the methods described here above in the specification, such as methods described in schemes 1 and 2.

In one embodiment, $R^7$ is $C_{1-4}$ alkyl in compounds (Ic) and (Id).

In another embodiment, $R^7$ is hydrogen in compounds (Ic) and (Id).

For example, when $R^7$ is hydrogen, compound of formula (Id) may be obtained by reacting compound of formula (IIa) wherein $R^2$ is n-propyl, hereafter referred to as compound of formula (IIb), with (S)-2-amino-butyramide.

Compound of formula (IIb) comprises a stereogenic center indicated by an asterisk. In one embodiment according to the present invention said stereogenic center is in (R)-form. Compound of formula (IIb) wherein stereogenic center is in (R)-form is referred to hereafter as compound of formula (IIc).

Reaction of compound of formula (IIc) with (S)-2-aminobutyramide affords a mixture of compound of formula (Id) and of compound of formula (Ie). Said mixture is decarboxylated according to conditions described here above in the specification to afford a mixture of brivaracetam and of compound (V) (scheme 3).

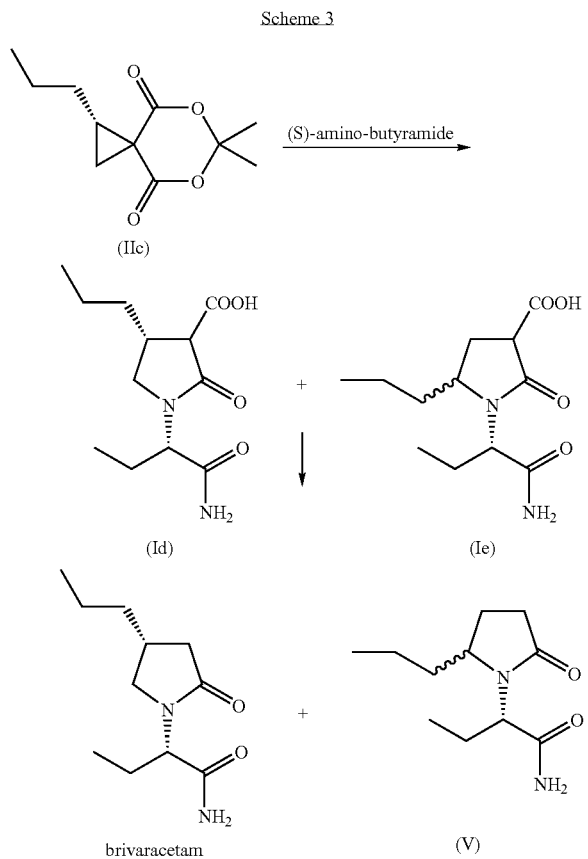

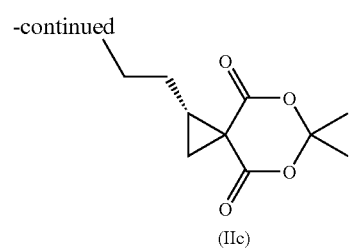

Compound (IId) may be synthesized according to any conventional method known to the man skilled in the art.

Generally, the overall process according to the invention and described here above in the specification does not require the use of toxic and expensive catalysts and thus may be advantageously applied on an industrial scale.

EXAMPLES

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Chemical names of compounds according to the present invention and mentioned in the present specification have been provided by Beilstein Autonom 2000 on MDL Crossfire V7.0 (© MDL Information Systems GmbH, Beilstein Institut zur Foerderung der Chemischen Wissenschaften).

NMR spectra are recorded on a Bruker 400 MHz spectrometer as solutions in deuterated chloroform ($CDCl_3$). Chemical shifts are expressed in parts per million (ppm, δ) downfield from tetramethylsilane and are referenced to the deuterated solvent ($CDCl_3$).

$^1$H NMR data were reported in the order of chemical shift, multiplicity (s, singlet; d, doublet; t, triplet; q, quartet; m, multiplet; app, apparent and/or multiple resonance), coupling constant (J) in hertz (Hz) and number of protons.

High Performance Liquid Chromatography (HPLC) spectra are recorded on an Alliance Waters 2695 equipped with a Sunfire C18 (3.5 um 2.1×150 mm) column. GRAD 90/10 is a gradient method in which the gradient ran from starting solvents composition (solvent A ($H_2O$, 80% v/v), solvent B ($CH_3CN$, 10% v/v) and solvent C($H_2O$+1% $H_3PO_4$ v/v, 10% v/v) to the final solvent composition (solvent A ($H_2O$, 0% v/v), solvent B ($CH_3CN$, 90% v/v) and solvent C($H_2O$+1% $H_3PO_4$ v/v, 10% v/v)) in 10 minutes and it is followed by a re-equilibration period of 5 minutes in the starting solvents composition.

Chiral HPLC are recorded on a Merck-Hitachi L-7100 equipped with a Daicel Chiralpak AD® 10 μm 250×4.6 mm. Eluent is a mixture of heptane/ethanol 50/50 with a flow of 1 ml/min.

Gas chromatography (GC) spectra are recorded on an Agilent 6890 series equipped with an Altech GC DB-5MS (15 m×0.25 mm) column. The oven is heated at 50° C. with a 1.5 mL/min helium flow and a FID detector heated at 300° C.

Chiral Gas chromatography spectra are recorded on an Agilent 6890 series equipped with a Chrompack Chirasil-DEX® CB 25 m×320 μm×1 μm column for compounds (VII) and (VIII) and with a Macherey—Nagel Lipodex® E 25 m×250 mm×1 mm column for compounds (IIc) and (IId). The oven is heated at 120° C. with a mL/min helium flow and a FID detector heated at 220° C.

Compounds (Id) and (Ie) may be esterified to afford corresponding esters according to conventional methods known to the person skilled in the art. Said esters may undergo a decarbalkoxylation according to conditions described here above in the specification.

Compound of formula (IIc) may be prepared, for example, according to the method described in general scheme 4.

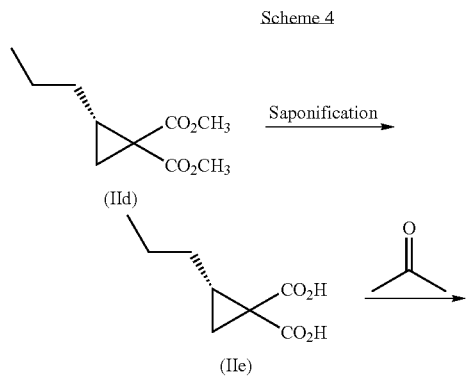

Mass spectroscopy (MS): API spectra were performed using a FINNIGAN (San Jose, Calif., USA) LCQ ion trap mass spectrometer. APCI source operated at 450° C. and the capillary heater at 160° C. The ESI source operated at 3.5 kV and the capillary heater at 21° C.

Example 1

Synthesis of Compounds of Formula (Ic)

1.a. Synthesis of 1-((S)-1-Carbamoyl-propyl)-2-oxo-pyrrolidine-3-carboxylic acid (compound of formula (Ic) wherein $R^7$ is hydrogen)

Compound (IIa) wherein $R^2$ is hydrogen (4 g, 23 mmol) and (S)-2-amino-butyramide (1.9 g, 19 mmol) in acetonitrile is refluxed for 12 hours. The reaction mixture is concentrated and the residue is diluted with $CH_2Cl_2$ (20 mL) and water (5 mL). The pH of the aqueous layer is adjusted to pH=1 with 37% HCl. The layers are separated. The aqueous phase is extracted with $CH_2Cl_2$ (2×10 mL), dried over anhydrous $MgSO_4$ and concentrated to give 3.18 g of compound (1c) wherein $R^4$ is hydrogen (14.8 mmol, 64%) as a white solid.

$^1$H NMR (250 MHz, DMSO): δ=12.9 and 12.0 (s, broad, 1H); 7.44 and 7.13 (2 s, broad, 1H); 6.97 (s, broad, 1H); 4.34 (dd, J=6.2, 1H); 3.67-3.00 (m+$H_2O$ signal, 3H); 2.38-2.04 (m, J=8.3, 2H); 1.79-1.48 (m, J=7.3, 2H); 0.80 (t, J=8.3, 3H).

1.b. Synthesis of 1-((S)-1-Carbamoyl-propyl)-2-oxo-pyrrolidine-3-carboxylic acid methyl ester (Ih) (compound of formula (Ic) wherein $R^7$ is methyl)

A solution of compound (1c) wherein $R^7$ is hydrogen (3.18 g, 14.8 mmol) in a 4.4N solution of HCl in methanol (6.7 mL) is stirred at room temperature for 3 hours. The reaction mixture is concentrated and the residue is diluted with water (20 mL) then extracted with $CH_2Cl_2$:IPA (9:1) (2×20 mL). The organic layer is evaporated to give 2 g of crude product that is purified by column chromatography (silicagel and $CH_2Cl_2$:MeOH:$NH_4OH$/94.5:5:0.5) to give 1.38 g of compound (1c) wherein $R^4$ is methyl (6.05 mmol, 41%).

$^1$H NMR (400 MHz, $CDCl_3$): δ=6.48 (s, broad, 1H); 5.76 (s, broad, 1H); 4.43 (m, 1H); 3.71 (s, 3H); 3.53-3.39 (m, 2H); 2.36-2.10 (m, 2H); 2.02 (m, 1H); 1.90 (m, 1H); 1.72-1.54 (m, 1H); 0.84 (m, 3H).

Example 2

Hydrolysis of 1-((S)-1-Carbamoyl-propyl)-2-oxo-pyrrolidine-3-carboxylic acid methyl ester (Ih)

A mixture of compound of formula (Ih) (1.1 g, 4.8 mmol), $K_2CO_3$ (0.99 g, 7.2 mmol), methanol (1 mL) and $H_2O$ (6 mL) is stirred at room temperature for 12 hours. The resulting aqueous solution is acidified to pH=2 with 6N HCl then extracted with $CH_2Cl_2$ (4×10 mL). The combined organic extracts are dried over anhydrous $MgSO_4$, filtered and concentrated to give compound of formula (Ic) wherein $R^4$ is hydrogen (1.05 g, 100%).

$^1$H NMR (250 MHz, DMSO): δ=12.9 and 12.0 (s, broad, 1H); 7.44 and 7.13 (2 s, broad, 1H); 6.97 (s, broad, 1H); 4.34 (dd, J=6.2, 1H); 3.67-3.00 (m+$H_2O$ signal, 3H); 2.38-2.04 (m, J=8.3, 2H); 1.79-1.48 (m, J=7.3, 2H); 0.80 (t, J=8.3, 3H).

Example 3

Decarboxylation of 1-((S)-1-Carbamoyl-propyl)-2-oxo-pyrrolidine-3-carboxylic acid (Ih)

A suspension of compound of formula (Ih) (1.40 g, 6.5 mmol) in MIBK (10 mL) is heated at 115-120° C. for 12 hours. The resulting solution is concentrated and the crude product is recrystallised in 4 volumes of toluene:acetone (1:1) to give 0.42 g of levetiracetam (2.5 mmol, 52%).

$^1$H NMR (400 MHz, $CDCl_3$): δ=6.28 (s, broad, 1H); 5.50 (s, broad, 1H); 4.46 (dd, J=8.8, J=7.1, 1H); 3.43 (m, 2H); 2.44 (m, 2H); 2.10-1.92 (m, 3H); 1.71 (m, 1H); 0.92 (t, J=7.5, 3H).

HPLC (method 90/10): Retention time=3.03 min (100%).
Chiral HPLC: Retention time=6.24 min (100%)
MS (APCI): 171 MH$^+$ Example 4

Decarbalkoxylation of 1-((S)-1-Carbamoyl-propyl)-2-oxo-pyrrolidine-3-carboxylic acid methyl ester (compound of formula (Ic) wherein $R^7$ is methyl)

A mixture of compound of formula (Ic) wherein $R^7$ is methyl (100 mg, 0.44 mmol), dimethylformamide (3 mL), $H_2O$ (15 drops) and NaCl (10 mg) is heated at 130-140° C. for 18 hours. The resulting mixture is diluted with saturated ammonium chloride (5 mL) and extracted with isopropyl acetate (2×10 mL). The combined organic extracts are dried over anhydrous $MgSO_4$, filtered and concentrated to give 75 mg (0.44 mmol, 100%) of levetiracetam.

$^1$H NMR (400 MHz, $CDCl_3$): δ=6.28 (s, broad, 1H); 5.50 (s, broad, 1H); 4.46 (dd, J=8.8, J=7.1, 1H); 3.43 (m, 2H); 2.44 (m, 2H); 2.10-1.92 (m, 3H); 1.71 (m, 1H); 0.92 (t, J=7.5, 3H).

HPLC (method 90/10): Retention time=3.03 min (100%).
Chiral HPLC Retention time=6.24 min (100%)
MS (APCI): 171 MH$^+$ Example 5

Synthesis of Brivaracetam

5a—Synthesis of (R)-12-pentanediol (VII)

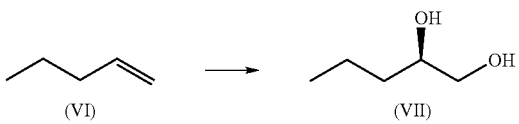

(VI)　　　　　(VII)

To a solution of AD-mix-β (25 g) in tert-butanol and water (1:1, 180 mL) at 0° C. is added 1-pentene (VI) (1.25 g, 17.86 mmol). The heterogenous slurry is stirred vigorously at 0° C. for 40 hours, then solid sodium sulfite (22.5 g) is slowly introduced at 0° C. The resulting suspension is allowed to warm to room temperature, stirred for an additional 1 hour, and diluted with $CH_2Cl_2$ (170 mL). The aqueous phase is extracted with $CH_2Cl_2$ (3×80 mL), and the combined organic extracts are dried over anhydrous $MgSO_4$, filtered and concentrated to give 1.68 g (16.15 mmol, 90%, ee=78.8%) of diol (VII) as a colorless oil.

$^1$H NMR (400 MHz, $CDCl_3$): δ=3.71 (s, broad, 1H); 3.64 (d, J=11.5, 1H); 3.42 (dd, J=10.9, J=7.8, 1H); 2.80-2.65 (m, broad, 2H); 1.52-1.31 (m, 4H); 0.94 (t, J=7.2, 3H).

GC: Rentention time=7.60 minutes (100%)
Chiral GC: Rentention time=4.97 minutes (ee=78.8%)

5b. Synthesis of (R)-4-Propyl-[1,3,2]dioxathiolane 2,2-dioxide (VIII)

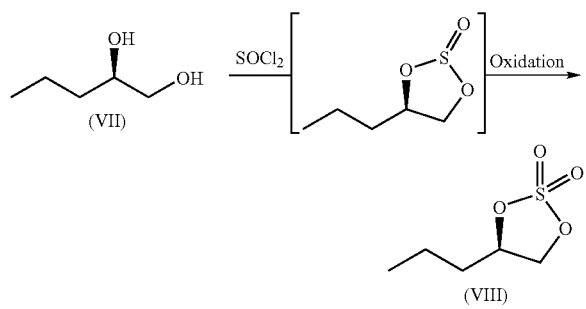

To a solution of (VII) (6.84 g, 65.70 mmol) in chloroform (66 mL) is added dropwise thionyl chloride (9.37 g, 79.0 mmol) at room temperature, and the resulting solution is refluxed for 1 hour. To a cooled reaction mixture is successively added acetonitrile (66 mL), $RuCl_3 \cdot xH_2O$ (10 mg), sodium periodate (21.3 g, 99.6 mmol) and water (100 mL). After stirring for 1.5 hours at room temperature, the resulting mixture is diluted with ether (500 mL). The organic layer is separated, successively washed with water (30 mL), saturated aqueous $NaHCO_3$ (2×30 mL) and brine (30 mL), dried over anhydrous $MgSO_4$, and concentrated to afford 11.74 g of sulfate (VIII) (65.70 mmol, 100%, ee=79.4%) as a colorless oil.

$^1$H NMR (400 MHz, $CDCl_3$): δ=4.99 (m, 1H); 4.71 (dd, J=8.4, J=6.1, 1H); 4.34 (t, J=8.4, 1H); 1.96 (m, 1H); 1.74 (m, 1H); 1.60-1.41 (m, 2H); 1.00 (t, J=7.6, 3H).

Chiral GC: Rentention time=14.50 minutes (ee=79.4%)

5c. Synthesis of (S)-2-Propyl-cyclopropane-1,1-dicarboxylic acid dimethyl ester (IId)

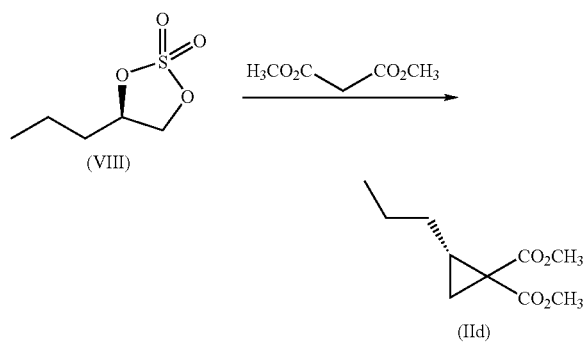

To a stirred suspension of NaH 60% (873 mg, 21.81 mmol) in dry 1,2-dimethoxyethane (48 mL) is added dropwise dimethyl malonate (1.31 g, 9.92 mmol) at room temperature over 10 minutes under a nitrogen atmosphere. A solution of (VIII) (1.82 g, 10.96 mmol) in dry 1,2-dimethoxyethane (5 mL) is added slowly to the malonate anion solution, and the resulting mixture is refluxed for 2 hours and then cooled to 0° C. After adding brine (30 mL), the mixture is extracted with diethyl ether (50 mL, 25 mL). The combined organic layers are dried over anhydrous $MgSO_4$, and concentrated under reduced pressure. The crude is purified by column chromatography (cyclohexane: EtOAc=90:10) to afford 1.28 g of (IId) (6.40 mmol, 65%, ee=78.2%) as a colorless oil.

$^1$H NMR (400 MHz, $CDCl_3$): δ=3.76 (s, 3H); 3.72 (s, 3H); 1.91 (m, 1H); 1.49-1.36 (m, 5H); 1.13 (m, 1H); 0.92 (t, J=6.9, 3H).

Chiral GC: Rentention time=5.90 minutes (ee=78.2%)

5d. Synthesis of (S)-2-Propyl-cyclopropane-1,1-dicarboxylic acid (IIe)

A solution of 2N aqueous sodium hydroxide (16 mL) is added dropwise to (IId) (1.27 g, 6.35 mmol) at room temperature. The resulting mixture is stirred 3 hours at room temperature then cooled to 0° C. and acidified to pH=1 with 37% HCl. The solution is extracted with $CH_2Cl_2$ (3×30 mL). The combined organic extracts are dried on anhydrous $MgSO_4$ and concentrated to afford 1.028 g of (IIe) (5.97 mmol, 94%).

$^1$H NMR (400 MHz, $CDCl_3$): δ=10.78 (s, broad, 2H); 2.24 (m, 1H); 2.07 (dd, J=9.2, J=4.2, 1H); 1.90 (dd, J=8.8, J=4.2, 1H); 1.69 (q, J=7.4, 2H); 1.43 (m, 2H); 0.93 (t, J=7.3, 3H).

5e. Synthesis of (S)-6,6-Dimethyl-1-propyl-5,7-dioxa-spiro[2.5]octane-4,8-dione (IIc)

To a solution of (IIe) (1.028 g, 5.97 mmol) in acetone (2 mL) at 0° C. is added successively $H_2SO_4$ (50 µL) and acetic anhydride (0.68 mL, 7.17 mmol). The reaction mixture is stirred for 1 hour at 0° C. then for 20 hours at room temperature. Acetone is evaporated and the residue is diluted with AcOiPr (20 mL) and water (5 mL). The pH of the aqueous layer is adjusted to pH=5 with saturated $NaHCO_3$. The layers are separated and the organic phase is washed with water (5 mL) and brine (5 mL), then dried over anhydrous $MgSO_4$, filtered and concentrated. The crude is purified by column chromatography (cyclohexane: EtOAc=70:30) to give 915 mg of (IIc) (4.32 mmol, 72%, ee=77.8%).

$^1$H NMR (400 MHz, $CDCl_3$): δ=2.25 (m, 2H); 1.94 (dd, J=8.0, J=2.8, 1H); 1.80 (s, 3H); 1.78 (s, 3H); 1.75-1.59 (m, 2H); 1.51-1.43 (m, 2H); 0.97 (t, J=7.4, 3H).

Chiral GC: Rentention time=22.25 minutes (ee=77.8%)

5f. Synthesis of (R)-1-((S)-1-Carbamoyl-propyl)-2-oxo-4-propyl-pyrrolidine-3-carboxylic acid (Id) and 1-((S)-1-Carbamoyl-propyl)-2-oxo-5-propyl-pyrrolidine-3-carboxylic acid (Ie)

A solution of (IIc) (636 mg, 3.0 mmol) and (S)-2-aminobutyramide (612 mg, 6.0 mmol) in acetonitrile is refluxed for 10 hours. The reaction mixture is concentrated and the residue is diluted with $CH_2Cl_2$ (20 mL) and water (5 mL). The pH of the aqueous layer is adjusted to pH=1 with 37% HCl. The layers are separated. The aqueous phase is extracted with $CH_2Cl_2$ (2×10 mL), dried over anhydrous $MgSO_4$ and concentrated to afford 570 mg of a mixture of (Id) and (Ie) (2.23 mmol, 74%) as a white solid.

$^1$H NMR (400 MHz, $CDCl_3$) of the mixture (Id) and (Ie): δ=7.14 (s, broad); 6.91 (s, broad); 6.85 (s, broad); 6.72 (s, broad); 6.59 (s, broad); 6.39 (s, broad); 6.21 (s, broad); 6.12 (s, broad); 4.57 (m); 4.43 (m); 4.15 (t, J=7.7); 4.03 (t, J=7.7); 3.78-3.47 (m); 3.20 (d, J=5.6); 3.16 (d, J=8.4); 3.03 (dd, J=10.0, J=4.6); 2.71-2.42 (m); 2.31-1.20 (m); 0.95 ($t_{app}$).

HPLC (method 90/10): Retention time=6.98 minutes
MS (ESI)=257 MH$^+$

5g. Synthesis of (R)-1-((S)-1-Carbamoyl-propyl)-2-oxo-4-propyl-pyrrolidine-3-carboxylic acid methyl ester (If) and 1-((S)-1-Carbamoyl-propyl)-2-oxo-5-propyl-pyrrolidine-3-carboxylic acid methyl ester (Ig)

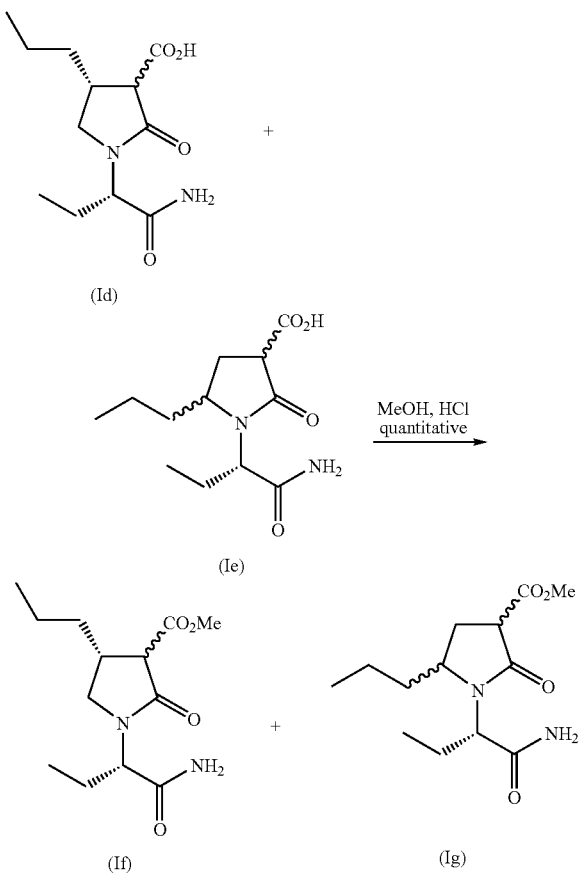

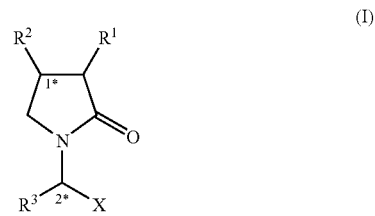

A 4.4N solution of hydrochloric acid in methanol (7.2 mL, 32 mmol) is added to a mixture of (Id) and (Ie) (4.1 g, 16 mmol). The reaction mixture is stirred 4 hours at room temperature then methanol is evaporated. The residue is diluted with water (10 mL) and extracted with toluene (20 mL). The organic layer is dried on anhydrous magnesium sulfate and evaporated. The crude is purified by column chromatography ($CH_2Cl_2$/MeOH/$NH_4OH$:97/2/1) to give 1.3 g (4.8 mmol, 30%) of a mixture of (If) and (Ig).

HPLC (method 90/10): Retention time=7.43 minutes, 7.88 minutes, 8.10 minutes, 8.20 minutes.
MS (ESI): 271 $MH^+$ 5h. Synthesis of brivaracetam and (V)

A suspension of (Id) and (Ie) (0.6 g, 2.3 mmol) in MIBK (10 mL) is heated at 120° C. for 6 hours. The resulting solution is concentrated and separated on chromatography column (Silicagel 60 0.068-0.200 mm, cyclohexane/EtOAc:10/90) to give 0.13 g of brivaracetam (0.6 mmol, 26%, ee=94%) and (V).

$^1$H NMR (400 MHz, $CDCl_3$): δ=6.17 (s, broad, 1H); 5.32 (s, broad, 1H); 4.43 (dd, J=8.6, J=7.1, 1H); 3.49 (dd, J=9.8, J=8.1, 1H); 3.01 (dd, J=9.8, J=7.1, 1H); 2.59 (dd, J=16.8, J=8.7, 11H); 2.34 (m, 1H); 2.08 (dd, J=16.8, J=7.9, 1H); 1.95 (m, 1H); 1.70 (m, 1H); 1.47-1.28 (m, 4H); 0.91 (dt, J=7.2, J=2.1, 6H).

HPLC (method 90/10): Retention time=7.78 minutes
Chiral HPLC: Retention time=9.66 minutes (97%)
MS (ESI):213 $MH^+$

The invention claimed is:
1. A compound of formula (I), or a geometrical isomer, enantiomer, or diastereoisomer thereof,

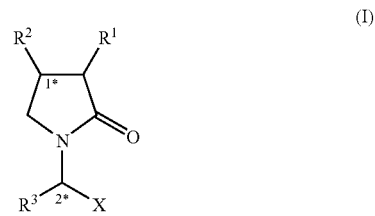

wherein,
$R^1$ is —COOH, —COOM or —$COOR^4$,
$R^2$ is hydrogen or $C_{1-10}$ alkyl,
$R^3$ is $C_{1-10}$ alkyl or $C_{2-6}$ alkenyl,
X is —$CONR^5R^6$, —COOH, —$COOR^4$ or —CN,
M is an alkali metal,
$R^4$ is $C_{1-10}$ alkyl,
$R^5$ is hydrogen or $C_{1-10}$ alkyl,
$R^6$ is hydrogen or $C_{1-10}$ alkyl,
1* and 2* denote a stereogenic center,
provided that compound of formula (I) is not 1-((1S)-1-carbamoyl-propyl)-2-oxo-pyrrolidone-3-carboxylic acid or 2(S)(3-carboxy-2-oxo-1-pyrrolidinyl)-4-methyl pentanoic acid methyl ester.
2. The compound of formula (I) according to claim 1 wherein $R^2$ is hydrogen or $C_{1-4}$ alkyl.
3. The compound of formula (I) according to claim 1 wherein $R^3$ is $C_{1-4}$ alkyl.
4. The compound of formula (I) according to claim 1 wherein $R^4$ is methyl.
5. The compound of formula (I) according to claim 1 wherein $R^1$ is —COOH.
6. The compound of formula (I) according to claim 1 wherein $R^2$ is hydrogen or n-propyl.
7. The compound of formula (I) according to claim 1 wherein $R^3$ is ethyl.
8. The compound of formula (I) according to claim 1 wherein X is —$CONH_2$.
9. The compound of formula (I) according to claim 1 wherein the stereogenic center indicated by (1*) is in the (R)-form.
10. The compound of formula (I) according to claim 1 wherein the stereogenic center indicated by (2*) is in the (S)-form.
11. The compound of formula (I) according to claim 1 selected from the group consisting of (R)-1-((S)-1-Carbamoyl-propyl)-2-oxo-4-propyl-pyrrolidine-3-carboxylic acid, 1-((S)-1-Carbamoyl-propyl)-2-oxo-pyrrolidine-3-carboxylic acid methyl ester and (R)-1-((S)-1-Carbamoyl-propyl)-2-oxo-4-propyl-pyrrolidine-3-carboxylic acid methyl ester.
12. A process for the preparation of a compound of formula (IV), a geometrical isomer, enantiomer, diastereoisomer, or pharmaceutically acceptable salt thereof, said process comprising decarboxylating a compound of formula (Ia), a geometrical isomer, enantiomer, or diastereoisomer thereof, (Ia)

wherein
R¹ is —COOH or —COOM,
R² is hydrogen or $C_{1-10}$ alkyl,
R³ is $C_{1-10}$ alkyl or $C_{2-6}$ alkenyl,
X is —CONR⁵R⁶, —COOH, —COOR⁴ or —CN,
M is an alkali metal,
R⁴ is $C_{1-10}$ alkyl,
R⁵ is hydrogen or $C_{1-10}$ alkyl,
R⁶ is hydrogen or $C_{1-10}$ alkyl.

13. A process for the preparation of a compound of formula (IV), a geometrical isomer, enantiomer, diastereoisomer, or pharmaceutically acceptable salt thereof, (IV)

said process comprising decarboalkoxylating a compound of formula (Ib)), a geometrical isomer, enantiomer, or diastereoisomer thereof, (Ib)

wherein
R² is hydrogen or $C_{1-10}$ alkyl,
R³ is $C_{1-10}$ alkyl or $C_{2-6}$ alkenyl,
X is —CONR⁵R⁶, —COOH, —COOR⁴ or —CN,
R⁴ is $C_{1-10}$ alkyl,
R⁵ is hydrogen or $C_{1-10}$ alkyl,
R⁶ is hydrogen or $C_{1-10}$ alkyl.

14. The process according to claim 12 wherein R² is hydrogen or $C_{1-4}$ alkyl.

15. The process according to claim 12 wherein R³ is $C_{1-4}$ alkyl.

16. The process according to claim 13 wherein R⁴ is methyl.

17. The process according to claim 12 wherein X is —CONH₂.

18. The process according to claim 12 wherein configuration of stereogenic centers 1* and 2* present in compounds of formula (I) is retained in compounds of formula (IV).

19. The process according to claim 12 wherein the stereogenic center indicated by (2*) in compounds of formula (Ia) and (IV) is in the (S)-form.

20. The process according to claim 12 which is performed in methylisobutylketone (MIBK).

21. The process according to claim 13 which is performed in methylisobutylketone (MIBK).

22. The process according to claim 12 which is performed at a temperature ranging from 110° C. to 130° C.

23. A process for the preparation of levetiracetam, said process comprising decarboxylating or decarbalkoxylating a compound of formula (Ic), (Ic)

wherein R⁷ is hydrogen, an alkali metal or $C_{1-10}$ alkyl.

24. A process for the preparation of brivaracetam, said process comprising decarboxylating or decaralkoxylating a compound of formula (Id), (Id)

wherein R⁷ is hydrogen, an alkali metal or $C_{1-10}$ alkyl.

25. The process according to claim 13 wherein $R^2$ is hydrogen or $C_{1-4}$ alkyl.

26. The process according to claim 13 wherein $R^3$ is $C_{1-4}$ alkyl.

27. The process according to claim 13 wherein X is —$CONH_2$.

28. The process according to claim 13 wherein configuration of stereogenic centers 1* and 2* present in compounds of formula (I) is retained in compounds of formula (IV).

29. The process according to claim 13 wherein the stereogenic center indicated by (2*) in compounds of formula (Ib) and (IV) is in the (S)-form.

30. The process according to claim 13 which is performed at a temperature ranging from 110° C. to 130° C.

* * * * *

UNITED STATES PATENT AND TRADEMARK OFFICE
CERTIFICATE OF CORRECTION

PATENT NO. : 8,076,493 B2  Page 1 of 1
APPLICATION NO. : 12/096257
DATED : December 13, 2011
INVENTOR(S) : Ates et al.

It is certified that error appears in the above-identified patent and that said Letters Patent is hereby corrected as shown below:

At claim 1, column 18, lines 33-35, replace "1-((1S)-1-carbamoyl-propyl)-2-oxo-pyrrolidone-3-carboxylic acid" with -- 1-((1S)-1-carbamoyl-propyl)-2-oxo-pyrrolidine-3-carboxylic acid --

Signed and Sealed this
Seventh Day of February, 2012

David J. Kappos
*Director of the United States Patent and Trademark Office*